United States Patent
Hibri et al.

(10) Patent No.: US 9,295,479 B2
(45) Date of Patent: Mar. 29, 2016

(54) SURGICAL DEVICE

(71) Applicant: Spinal Stabilization Technologies, LLC, Austin, TX (US)

(72) Inventors: Nadi Salah Hibri, San Antonio, TX (US); James Douglas Lutz, San Antonio, TX (US)

(73) Assignee: SPINAL STABILIZATION TECHNOLOGIES, LLC, San Antonio, TX (US)

( * ) Notice: Subject to any disclaimer, the term of this patent is extended or adjusted under 35 U.S.C. 154(b) by 422 days.

(21) Appl. No.: 13/831,355

(22) Filed: Mar. 14, 2013

(65) Prior Publication Data

US 2014/0276832 A1    Sep. 18, 2014

(51) Int. Cl.
*A61B 17/3207*    (2006.01)
*A61B 17/16*    (2006.01)
(Continued)

(52) U.S. Cl.
CPC ......... *A61B 17/1671* (2013.01); *A61B 17/1633* (2013.01); *A61B 17/1642* (2013.01); *A61B 17/1644* (2013.01); *A61B 17/32002* (2013.01); *A61B 17/320783* (2013.01); *A61B 2017/00261* (2013.01); *A61B 2017/00685* (2013.01); *A61B 2017/320775* (2013.01); *A61B 2017/320791* (2013.01)

(58) Field of Classification Search
CPC ....... A61B 2017/320791; A61B 2017/320775; A61B 17/320783
USPC ................................. 606/79–86 B
See application file for complete search history.

(56) References Cited

U.S. PATENT DOCUMENTS

| 3,875,595 A | 4/1975 | Froning |
| 5,192,326 A | 3/1993 | Bao et al. |

(Continued)

FOREIGN PATENT DOCUMENTS

| CA | 2574977 | * | 7/2005 |
| KR | 20120040309 A | | 4/2012 |
| WO | WO2007/087404 A2 | | 8/2007 |

OTHER PUBLICATIONS

Birkenmaier et al., Minimally Invasive Endoscopic Spinal Surgery, www.spineuniverse.com/displayarticle.pho/article_2016.html [Jun. 15, 2009].

(Continued)

*Primary Examiner* — David Bates
(74) *Attorney, Agent, or Firm* — Norton Rose Fulbright US LLP

(57) ABSTRACT

An exemplary nucleus removal device may be used to remove a portion of nucleus pulposus from an intervertebral disc. A nucleus removal device may include a cannula, an access tool, a maceration tool, and an evacuation tool. The access cannula is inserted into an intervertebral body laterally, creating a fissure in the annular fibrosis. The access tool 304 is slid through the access cannula and the fissure in annular fibrosis, such that a portion of access tool extends into the nucleus pulposus. The maceration tool is extended from the access tool into the nucleus pulposus, in a direction orthogonal to the axial extension of access tool, and macerates the nucleus pulposus. To assist in maceration, a stream of liquid may also be introduced into the vertebral body through the access tool before, during, or after maceration. Macerated material and liquid is removed from the intervertebral disc by the evacuation tool.

16 Claims, 10 Drawing Sheets

(51) Int. Cl.
*A61B 17/32* (2006.01)
*A61B 17/00* (2006.01)

(56) References Cited

U.S. PATENT DOCUMENTS

| | | | |
|---|---|---|---|
| 5,269,798 A * | 12/1993 | Winkler | A61B 17/32002 30/345 |
| 5,439,464 A | 8/1995 | Shapiro | |
| 5,571,189 A | 11/1996 | Kuslich | |
| 5,591,170 A * | 1/1997 | Spievack | A61B 17/14 30/122 |
| 5,645,597 A | 7/1997 | Krapiva | |
| 5,674,295 A | 10/1997 | Ray et al. | |
| 5,702,449 A | 12/1997 | McKay | |
| 5,792,167 A * | 8/1998 | Kablik | A61B 17/32002 604/22 |
| 5,865,845 A | 2/1999 | Thalgott | |
| 5,888,220 A | 3/1999 | Felt et al. | |
| 5,890,268 A | 4/1999 | Mullen et al. | |
| 5,981,826 A | 11/1999 | Ku et al. | |
| 5,990,378 A | 11/1999 | Ellis | |
| 6,127,597 A | 10/2000 | Beyer et al. | |
| 6,264,695 B1 | 7/2001 | Stoy | |
| 6,332,894 B1 | 12/2001 | Stalcup et al. | |
| 6,375,682 B1 | 4/2002 | Fleischmann et al. | |
| 6,390,992 B1 | 5/2002 | Morris et al. | |
| 6,395,032 B1 | 5/2002 | Gauchet | |
| 6,419,704 B1 | 7/2002 | Ferree | |
| 6,436,143 B1 | 8/2002 | Ross et al. | |
| 6,440,138 B1 * | 8/2002 | Reiley | A61B 17/1671 606/45 |
| 6,482,234 B1 | 11/2002 | Weber et al. | |
| 6,527,804 B1 | 3/2003 | Gauchet et al. | |
| 6,596,008 B1 | 7/2003 | Kambin | |
| 6,712,853 B2 | 3/2004 | Kuslich | |
| 6,733,532 B1 | 5/2004 | Gauchet et al. | |
| 6,846,314 B2 * | 1/2005 | Shapira | A61B 10/025 604/35 |
| 6,852,095 B1 | 2/2005 | Ray | |
| 6,863,676 B2 * | 3/2005 | Lee | A61B 10/0266 600/567 |
| 6,866,681 B2 | 3/2005 | Laboureau et al. | |
| 6,893,466 B2 | 5/2005 | Trieu | |
| 6,958,077 B2 | 10/2005 | Suddaby | |
| 6,969,404 B2 | 11/2005 | Ferree | |
| 7,001,431 B2 | 2/2006 | Bao et al. | |
| 7,004,971 B2 | 2/2006 | Serhan et al. | |
| 7,008,427 B2 | 3/2006 | Sevrain | |
| 7,056,345 B2 | 6/2006 | Kuslich | |
| 7,077,865 B2 | 7/2006 | Bao et al. | |
| 7,133,001 B2 | 11/2006 | Mrstik et al. | |
| 7,182,783 B2 | 2/2007 | Trieu | |
| 7,201,751 B2 | 4/2007 | Zucherman et al. | |
| 7,201,776 B2 | 4/2007 | Ferree et al. | |
| 7,204,851 B2 | 4/2007 | Trieu et al. | |
| 7,220,282 B2 | 5/2007 | Kuslich | |
| 7,273,497 B2 | 9/2007 | Ferree | |
| 7,309,359 B2 | 12/2007 | Trieu et al. | |
| 7,632,294 B2 | 12/2009 | Milbodker et al. | |
| 7,722,612 B2 | 5/2010 | Sala et al. | |
| 7,842,055 B2 | 11/2010 | Pintor et al. | |
| 7,972,351 B2 | 7/2011 | Trinidad | |
| 7,993,351 B2 | 8/2011 | Worley et al. | |
| 8,066,758 B2 | 11/2011 | Bogert et al. | |
| 8,133,250 B2 | 3/2012 | Parsonage et al. | |
| 8,142,489 B2 | 3/2012 | Doran et al. | |
| 2002/0026244 A1 | 2/2002 | Trieu | |
| 2002/0147497 A1 | 10/2002 | Belef et al. | |
| 2002/0183758 A1 * | 12/2002 | Middleton | A61B 17/1617 606/79 |
| 2003/0028251 A1 | 2/2003 | Mathews | |
| 2003/0199979 A1 | 10/2003 | McGuckin, Jr. | |
| 2004/0106999 A1 | 6/2004 | Mathews | |
| 2004/0186471 A1 | 9/2004 | Trieu | |
| 2004/0230309 A1 | 11/2004 | DiMauro et al. | |
| 2005/0015150 A1 | 1/2005 | Lee | |
| 2005/0055099 A1 | 3/2005 | Ku | |
| 2005/0065609 A1 | 3/2005 | Wardlaw | |
| 2005/0090901 A1 | 4/2005 | Studer | |
| 2005/0197702 A1 | 9/2005 | Coppes et al. | |
| 2005/0209610 A1 * | 9/2005 | Carrison | A61B 17/1671 606/114 |
| 2005/0209622 A1 * | 9/2005 | Carrison | A61B 17/1671 606/170 |
| 2005/0251259 A1 | 11/2005 | Suddaby | |
| 2005/0261692 A1 * | 11/2005 | Carrison | A61B 17/1631 606/79 |
| 2005/0278029 A1 | 12/2005 | Trieu | |
| 2006/0004369 A1 * | 1/2006 | Patel | A61B 17/1633 606/79 |
| 2006/0247780 A1 | 11/2006 | Bert | |
| 2006/0293749 A1 | 12/2006 | Hudgins et al. | |
| 2007/0060924 A1 | 3/2007 | Choi | |
| 2007/0073402 A1 | 3/2007 | Vresilovic | |
| 2007/0093906 A1 | 4/2007 | Hudgins | |
| 2007/0135921 A1 | 6/2007 | Park | |
| 2007/0150061 A1 | 6/2007 | Trieu | |
| 2007/0162136 A1 | 7/2007 | O'Neil et al. | |
| 2007/0168031 A1 | 7/2007 | Hudgins et al. | |
| 2007/0173935 A1 | 7/2007 | O'Neil et al. | |
| 2007/0173940 A1 | 7/2007 | Hestad et al. | |
| 2007/0213732 A1 | 9/2007 | Khanna et al. | |
| 2007/0239182 A1 * | 10/2007 | Glines | A61B 17/22012 606/159 |
| 2007/0255406 A1 | 11/2007 | Trieu | |
| 2007/0270953 A1 | 11/2007 | Trieu | |
| 2008/0046082 A1 | 2/2008 | Lee | |
| 2008/0058932 A1 | 3/2008 | Trieu et al. | |
| 2008/0097499 A1 * | 4/2008 | Nash | A61B 17/320758 606/159 |
| 2008/0114364 A1 * | 5/2008 | Goldin | A61B 17/1617 606/79 |
| 2008/0154367 A1 | 6/2008 | Justis | |
| 2008/0154368 A1 | 6/2008 | Justis et al. | |
| 2008/0154373 A1 | 6/2008 | Protopsaltis et al. | |
| 2008/0183175 A1 * | 7/2008 | Saal | A61B 17/320783 606/84 |
| 2008/0288074 A1 | 11/2008 | O'Neil et al. | |
| 2009/0012618 A1 | 1/2009 | Ahrens et al. | |
| 2009/0105740 A1 * | 4/2009 | Lee | A61B 17/14 606/177 |
| 2009/0112323 A1 | 4/2009 | Hestad et al. | |
| 2010/0030216 A1 | 2/2010 | Arcenio | |
| 2010/0256619 A1 | 10/2010 | Teitelbaum et al. | |
| 2010/0256766 A1 | 10/2010 | Hibri et al. | |
| 2011/0190753 A1 | 8/2011 | Forrest | |
| 2011/0196499 A1 | 8/2011 | Boucher et al. | |
| 2011/0264224 A1 | 10/2011 | Ferree | |
| 2012/0089229 A1 | 4/2012 | Thramann | |
| 2012/0277862 A1 | 11/2012 | Tornier et al. | |

OTHER PUBLICATIONS

Sharma et al., "Manufacturing of Doubly Curved Tubular Composite Structures: Mapping and Weave Modifications", > Thermoplastic Composite Materials, 15:209-225 (May 2002).

Wu et al., The direct effect of graft compliance mismatch per se on development of host arterial intimal hyperplasia at the anastomotic interface, Annals of Vascular Surgery, 7(2):156-168 (Mar. 1993).

Viscocliosi et al., "Beyond Total Disc: The Future of Spine Surgery", Spine Non-Fusion, Musculoskeletal Investment Research, pp. 1-289 (May 2004).

International Search Report dated Jun. 25, 2014 for International Application No. PCT/US2014/019957, filed Mar. 3, 2014.

International Search Report dated Jun. 17, 2014 for International Application No. PCT/US2014/019911, filed Mar. 3, 2014.

International Search Report dated Jun. 19, 2014 for International Application No. PCT/US2014/019887, filed Mar. 3, 2014.

* cited by examiner

SURGICAL DEVICE

TECHNICAL FIELD

This invention relates to surgical tools, and more particularly to surgical tools used to remove tissue from the body and implant prosthetic devices.

BACKGROUND

The human vertebral column is a vital part of the human physiology that houses and protects the spinal cord, and provides structural support for the body. In a typical human, the vertebral column is made up of twenty-four articulating vertebrae and nine fused vertebrae, and is generally divided into several regions, including the cervical, thoracic, sacral, and coccygeal regions.

While variations exist between each vertebra depending on its location and region, vertebrae generally consist of a body, pedicles, a lamina, a spinous process, transverse processes, facet joints, and a spinal canal, each of which play a pivotal role in providing the overall supportive and protective functionality of the vertebral column. Of these features, the vertebral body is of particular importance in providing support. The vertebral body is the largest portion of the vertebra, provides an attachment point of intervertebral discs, protects the spinal cord, and bears the majority of the load of the vertebra.

Each vertebra is separated from an adjacent vertebra by an intervertebral disc, a cartilaginous joint that acts as a ligament to hold the vertebrae together. A disc consists of an outer annulus fibrosus which surrounds the inner nucleus pulposus. The annulus fibrosus consists of several layers of fibrocartilage which contain the nucleus pulposus and distribute pressure evenly across the disc. The nucleus pulposus contains loose fibers suspended in a mucoprotein gel. The nucleus of the disc acts as a shock absorber, absorbing the impact of the body's daily activities and keeping the two vertebrae separated.

While the intervertebral disc protects adjacent vertebral bodies from impact or contact, various disorders may compromise the structure of the discs and negatively impact their functionality. For example, due to age, the nucleus pulposus may dehydrate and deform, or the annulus fibrosus may weaken and become more prone to tearing. Discs may also be damaged through trauma, resulting in undesirable bulging or loss of nucleus pulposus through a fissure. These disc disorders may diminish a disc's ability to absorb shock and transfer loads, or cause adjacent discs to contact, possibly resulting in acute or chronic pain for those suffering from these disorders.

Intervertebral disc disorders are frequently treated by removing portions of the disk or the entire disc and fusing adjacent vertebrae to prevent relative movement between the adjacent vertebrae. In other treatments, portions of the disc or the entire disc are removed and replaced with a prosthetic device. As these prostheses commonly replace diseased or damaged tissue, it is often necessary to surgically remove the existing tissue from the vertebra before implantation of the prostheses in order to clear away damaged tissue and to make room for the implant. Prosthetic procedures often involve mechanical prosthetics that replace the entire disc but do not provide the range of motion or stability of the natural healthy disc. Moreover, removal of all or part of the disc material can negatively impact the end plates of the vertebrae.

Current surgical techniques to repair intervertebral discs often involve invasive techniques that disturb otherwise healthy tissue adjacent the intervertebral disk. It would be desirable to treat diseased or damaged intervertebral discs by leaving the annulus fibrosus largely intact and undisturbed while restoring the stability and mobility of the native intervertebral disc.

Ideally, a tool to remove the tissue from within an intervertebral disc should be compatible with existing percutaneous surgical procedures, such that the tool is minimally invasive during insertion and use. The tool should also be adapted to adjustably access and remove tissue from a broad region of the intervertebral disc from a single insertion point, such that diseased tissue can be removed without requiring surgical insertion at multiple points and without requiring twisting or torquing that may undesirably damage healthy tissue. The tool should also perform several functions related to tissue removal, such that the number of tools that must be simultaneously inserted is reduced.

SUMMARY

This specification describes technologies relating to the removal of tissue from the body. Implementations of the technology described herein comprise a surgical device that is inserted through a small surgical incision into a portion of the body, from which tissue is removed, and a method by which the device is used for removing tissue from a the body.

Various implementations of the present invention provide benefits that are desirable for surgical applications. The device is compatible with existing percutaneous surgical procedures, as it can be inserted, operated, and removed from the body through a single small incision. As such, operation of the device removes tissue from within the body with minimal damage to healthy surrounding structures. The device is also adapted to remove tissue from a broad region from a single insertion point without requiring the device to be twisted or torqued, reducing the damage to the outermost regions of the body. The device also combines several tools of various functions into a form factor, such as a tissue maceration tool, an evacuation tool, and a liquid injector. As such, the device can perform several functions that might otherwise require several different tools, thereby reducing the complexity of the procedure and reducing the number of incisions required to conduct the procedure. The device is also adjustable to operate over a wide range of physical dimensions, such that a single tool is compatible with a variety of different patients.

In one example embodiment an apparatus comprises: an axially extending tubular access tool, comprising a proximal first end having a first orifice along the axial extension of the tool, a distal second end, forming a point along the axial extension of the tool, a second orifice, formed between the first end and the second end and located on an axis orthogonal to the axial extension of the cannula, a first tubular channel extending from the first orifice to the second orifice, adapted to channel a liquid from the first access hole to the second access hole, a second tubular channel extending from the first orifice to the second orifice and in cooperative arrangement with a maceration tool, a third tubular channel extending from the first orifice to the second orifice and in cooperative arrangement with an evacuation tool; a maceration tool within the second channel, comprising a maceration element and a first axially extending shaft, wherein radial rotation of the first shaft results in rotation of the maceration element; an evacuation tool within the third channel, comprising one or more evacuation elements and a second axially extending shaft, wherein radial rotation of the second shaft results in rotation of the cavitation element; wherein movement of the first shaft in a proximal to distal direction results in movement of the maceration element out of the second orifice in a direction orthogonal to the longitudinal extension of the cannula; wherein the maceration element is adapted to macerate tissue when rotated; and wherein the evacuation elements are adapted to move material through the third channel when rotated.

In another example embodiment of the present invention a method for removing tissue from the body comprises: inserting a cannula into the body; inserting a tissue removal device into the body, the device comprising a macerating tool, an evacuation tool, and an injection tool; macerating tissue by engaging the macerating tool; injecting liquid by engaging the injection tool; and removing tissue by engaging the evacuating tool.

In yet another example embodiment, implementations of the present invention may include one or more of the following features. The apparatus includes an axially extending access cannula, comprising a distally located first end, forming a first access hole along the axial extension of the cannula, a proximally located second end, forming a second access hole along the cannula, a tubular channel extending form the first access hole of the cannula to the second access hole of the cannula, and wherein the tubular channel of the cannula is adapted to hold the access tool. The maceration tool is self-expanding. The first or second shaft is connected to a motorized drive. The channel is connected to a liquid pump. An axial cross section of the cannula is of a generally polygonal, ovular, circular, or elliptical shape. The device comprises a surgically compatible material. The device of the apparatus comprises a radiopaque material. The cannula is adapted to percutaneously insert into an intervertebral disc.

Additional exemplary implementations of the present invention comprise various components of a surgical kit for accessing portions of the intervertebral disc, removing or displacing tissue, and delivering and implanting a prosthetic device. The kit in one exemplary embodiment comprises an access and delivery cannula, a nucleotomy tool for removal of the nucleus pulposus, a delivery and inflation stylus for delivering an inflatable prosthetic implant, and an inflatable prosthetic disc implant. An exemplary method of using an implementation of the present invention comprises penetrating the annulus fibrosus and accessing the nucleus pulposus of an intervertebral disk using an access and delivery cannula; delivering through the access cannula a nucleotome that is configured to allow the removal of the nucleus fibrosis from the intervertebral disc while leaving the annulus fibrosus substantially intact; maneuvering the nucleotome within the annulus fibrosus to remove the nucleus pulposus; removing the nucleotome; delivering a folded and deflated prosthetic implant through the access and delivery cannula and through the annulus fibrosus into the void formerly occupied by the nucleus pulposus; inflating the prosthetic implant using an inflation stylus wherein the prosthetic implant is inflated with at least two mediums including a gas and a curable silicon; and removing the inflation stylus and the access and delivery cannula.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The following specification describes various exemplary embodiments of the invention. The description is not to be taken in a limiting sense, but is made for the purpose of illustrating the general principles of the invention. Various inventive features are described below that can each be used independently of one another or in combination with other features.

Exemplary implementations of the present invention comprise various components of a surgical kit for accessing portions of the intervertebral disc, removing or displacing tissue, and delivering and implanting a prosthetic device. The kit in one exemplary embodiment comprises an access and delivery cannula, a nucleotomy tool for removal of the nucleus pulposus, a delivery and inflation stylus for delivering an inflatable prosthetic implant, and an inflatable prosthetic disc implant. An exemplary method of using an implementation of the present invention comprises penetrating the annulus fibrosus and accessing the nucleus pulposus of an intervertebral disk using an access and delivery cannula; delivering through the access cannula a nucleotome that is configured to allow the removal of the nucleus fibrosis from the intervertebral disc while leaving the annulus fibrosus substantially intact; maneuvering the nucleotome within the annulus fibrosus to remove the nucleus pulposus; removing the nucleotome; delivering a folded and deflated prosthetic implant through the access and delivery cannula and through the annulus fibrosus into the void formerly occupied by the nucleus pulposus; inflating the prosthetic implant using an inflation stylus wherein the prosthetic implant is inflated with at least two mediums including a gas and a curable silicon; and removing the inflation stylus and the access and delivery cannula.

Various aspects of the present invention, for example, implementations of the access and delivery cannula, inflation stylus and the prosthetic implant are disclosed in U.S. patent application Ser. No. 13/831,257, entitled "Prosthetic Spinal Disk Nucleus", filed concurrently with this application and incorporated herein by reference in its entirety.

Other aspects of the present invention, including an example inflatable prosthetic implant are disclosed in U.S. Patent Application Pub. No. US 2010/0256766, entitled Percutaneous Implantable Nuclear Prostheses and filed, Apr. 2, 2010, is incorporated herein by reference in its entirety.

An embodiment of the invention provides a surgical tool for removing tissue from the body, such as removing nucleus pulposus from an intervertebral disc. Broadly the tool includes an access and delivery cannula through which a nucleotome can be delivered. The nucleotome includes one or more passages to provide irrigation, suction and a flexible agitation tool.

Figure 1:
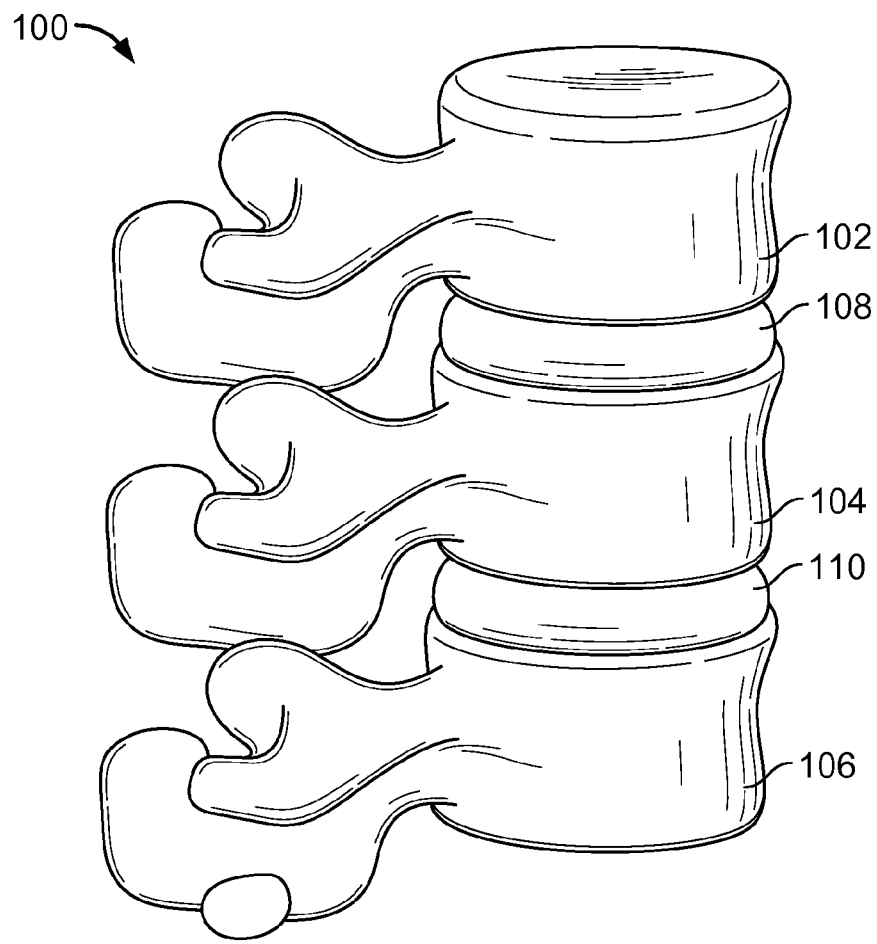
FIG. 1 is a perspective view of a portion of a human vertebral column.
Figure 2:
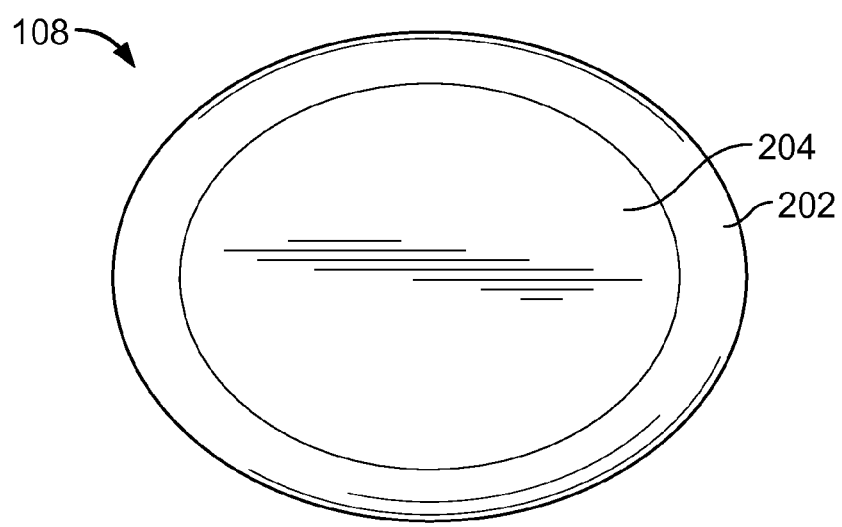
FIG. 2 is a cross-sectional view of a human intervertebral disc.

FIGS. 1-2 illustrate a portion of a typical human vertebral column. A vertebral column 100 is made up of several vertebral bodies 102, 104, and 106 separated by intervertebral discs 108 and 110. Intervertebral disc 108 is made up of an annular fibrosis 202 surrounding a region of nucleus pulposus 204.

Figure 3:
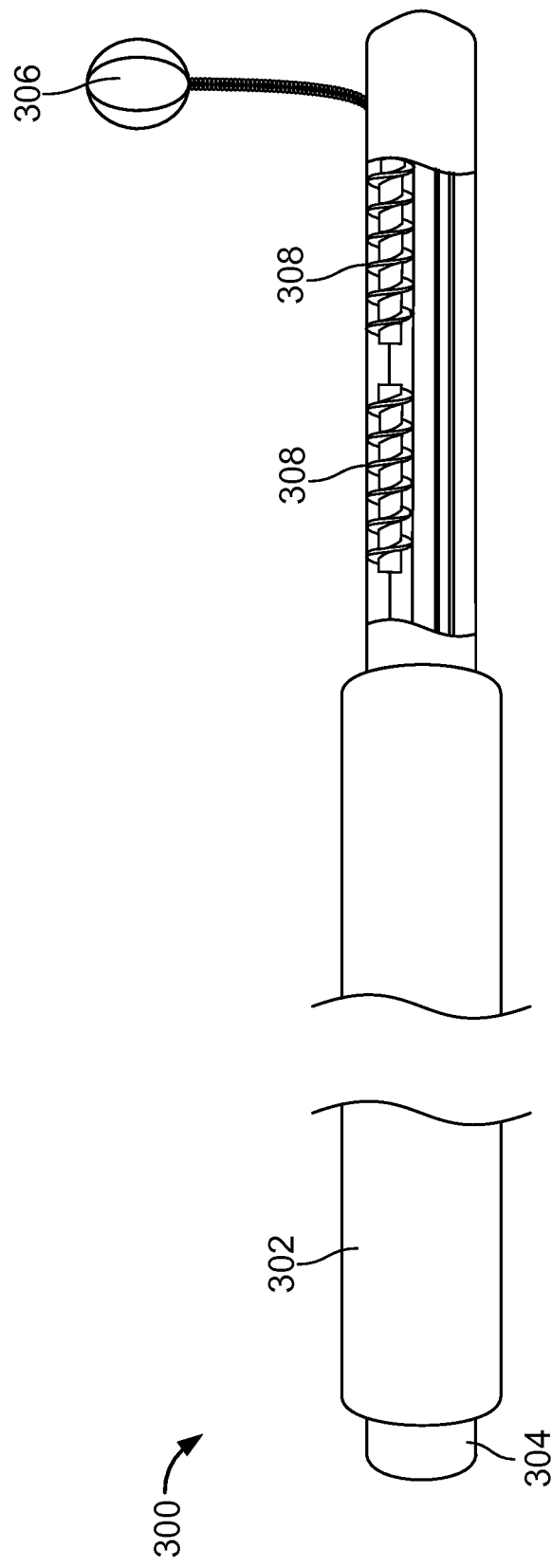
FIG. 3 is a perspective view of an embodiment of a nucleus removal tool.

FIG. 3 illustrates an exemplary nucleus removal device 300 used to remove a portion of nucleus pulposus 204 from intervertebral disc 108. Nucleus removal device 300 includes a cannula 302, a nucleotomy tool 304, a maceration element 306, and an evacuation element 308.

Figure 4A:
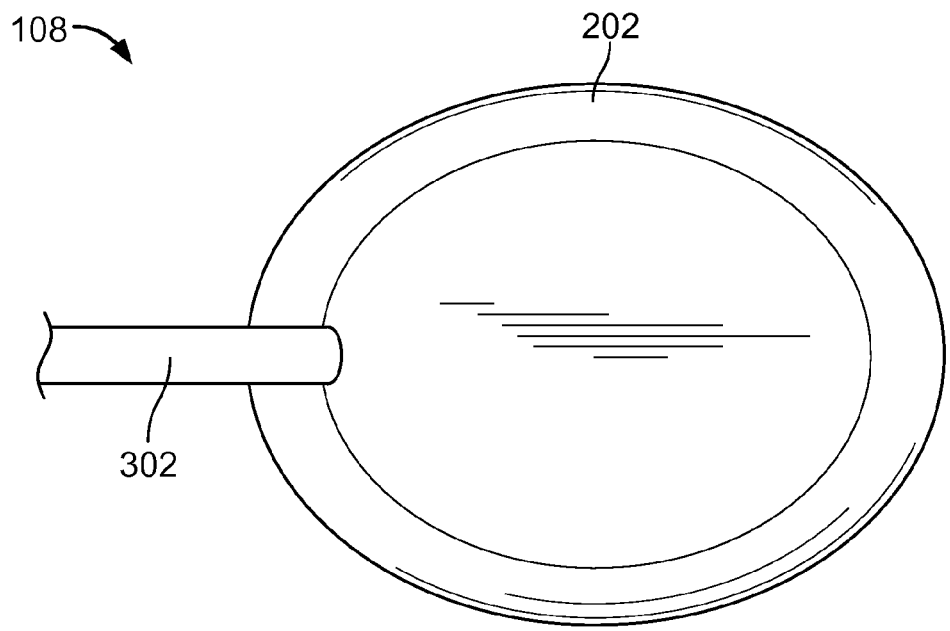
FIGS. 4A-C illustrate an example use of an exemplary access cannula, access tool, evacuation tool, and cavitation tool to removal nucleus pulposis from an intervertebral disc.
Figure 4B:
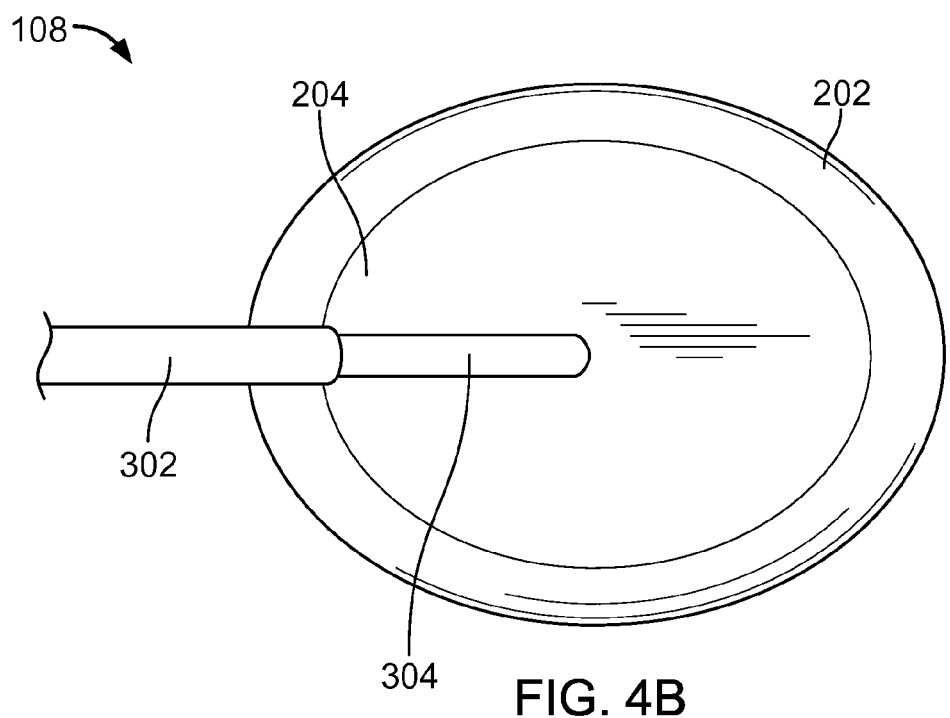
Figure 4C:
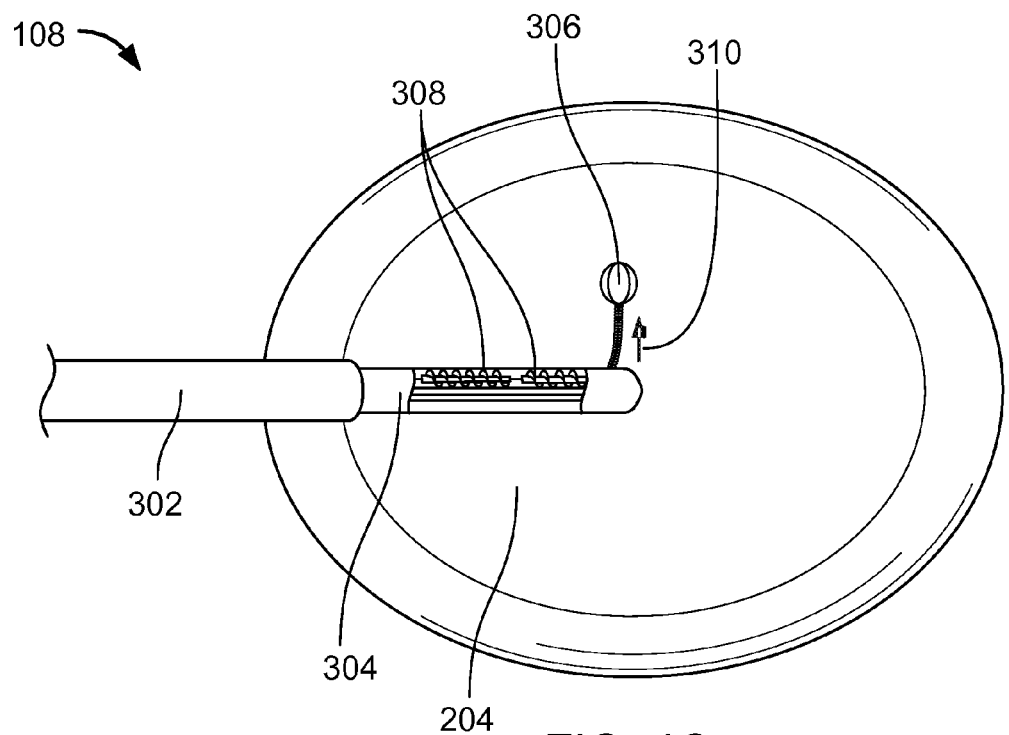

FIG. 4 depicts an exemplary usage of nucleus removal device 300. Referring to FIG. 4A, access cannula 302 is inserted into intervertebral body 108, creating a fissure in annular fibrosis 202. In FIG. 4B, nucleotomy tool 304 fits within and slides through access cannula 302 and the fissure in annular fibrosis 202, such that a portion of nucleotomy tool 304 extends into nucleus pulposus 204. In FIG. 4C, maceration element 306 is extended from nucleotomy tool 304 into the nucleus pulposus 204, in a direction generally orthogonal to the axial extension of nucleotomy tool 304, and macerates nucleus pulposus 204. To assist in maceration, irrigation may be provided through an irrigation channel in nucleotomy tool. A stream of irrigating liquid 310 may also be introduced into the vertebral body through the access tool before, during, or after maceration. Macerated material and liquid is removed from intervertebral disc 108 by evacuation element 308.

Figure 5:
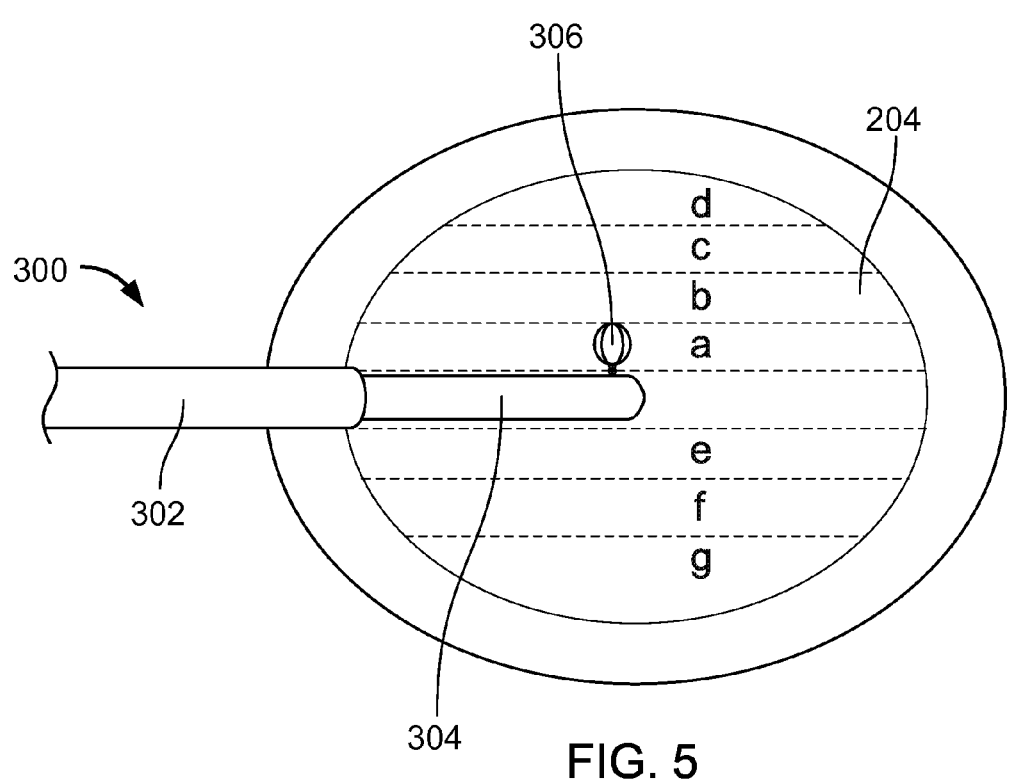
FIG. 5 illustrates the extension and retraction of an embodiment of a nucleus removal tool.

During maceration, nucleus removal device 300 is adjusted such that a broad region of nucleus pulposus 204 is macerated and evacuated. Referring to FIG. 5, nucleotomy tool 304 may be moved axially through cannula 302 during continuous operation such that maceration tool 306 contacts and macerates a volume of nucleus pulposus 204 extending parallel to the axial extension of the nucleotomy tool 304 (region a). Maceration tool 306 may also be extended in a direction generally orthogonal to the axial extension of the access tool 306, such that it may access a more radially distant volume of nucleus pulposus 204 (regions b-d). Nucleotomy tool 304 may also be rotated about its axis of extension, such that maceration tool 306 may interact with annular volumes of nucleus pulposus 204 (a and e, b and f, c and g). In this manner, maceration tool 306 may contact and macerate substantial portions of nucleus pulposus 204 from a single surgical insertion point. Maceration tool 306 may also be refracted prior to rotation of access tool 304, such that maceration is limited substantially to two dimensions.

During adjustment and operation of nucleotomy tool 304 and maceration tool 306, liquid stream 310 may be continuously applied, and liquid and macerated tissue may be continuously removed by evacuation element 308.

Upon completion of the procedure, maceration tool 306 is retracted into nucleotomy tool 304, and nucleotomy tool 304 is retracted into cannula 302. Cannula 302 can be subsequently removed from intervertebral disc 108 and from the body. In other embodiments, cannula 302 can remain in place and used for delivery of other surgical instruments, such as, for example, the delivery of a prosthetic implant and tools for inflation and placement of the implant within the intervertebral disc.

Figure 6:
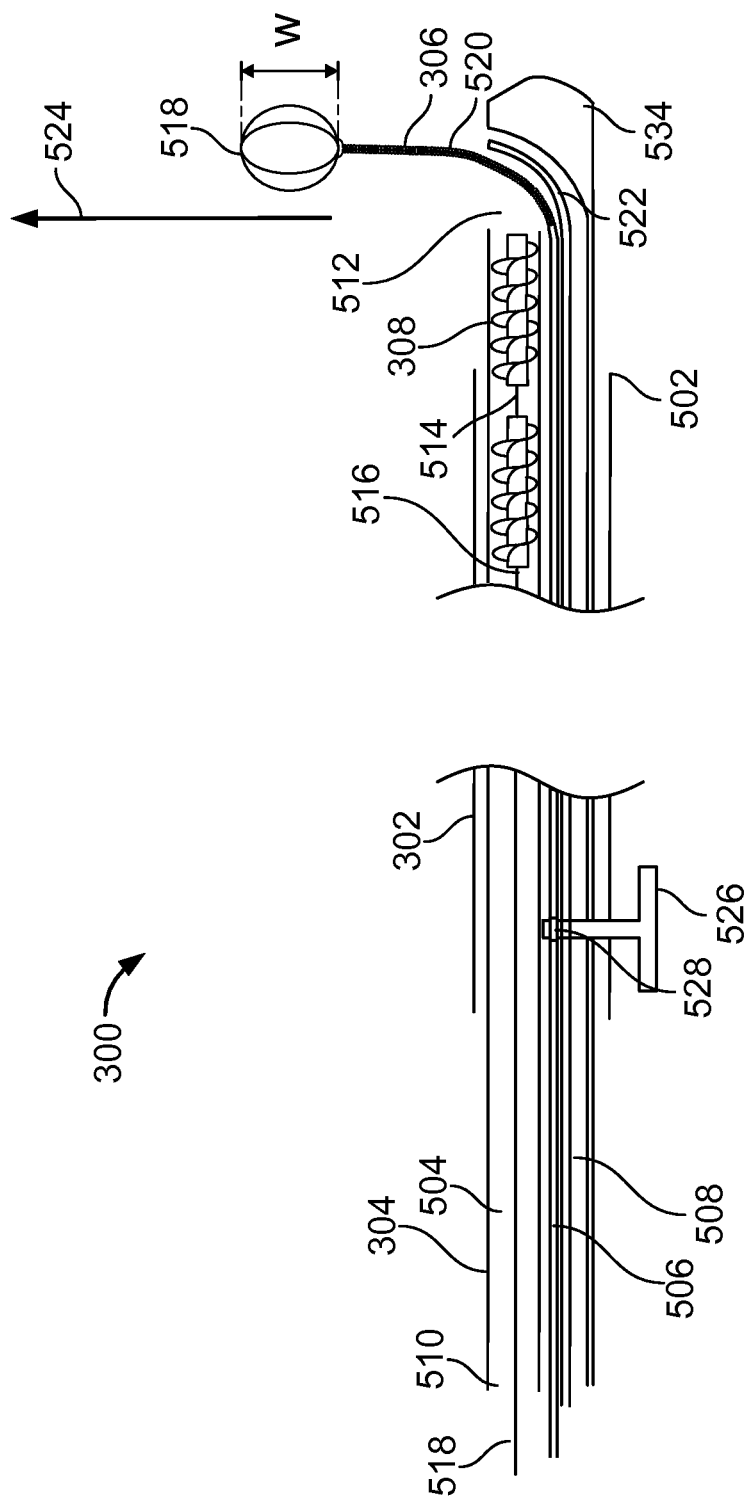
FIG. 6 illustrates a cross-sectional view of an embodiment of access tool.

FIG. 6 illustrates a cross-section of an exemplary embodiment of nucleus removal tool 300. Nucleus removal tool 300 includes cannula 302, nucleotomy tool 304, maceration element 306, and evacuation element 308. Cannula 302 is illustrated as an axially extending tube, adapted to hold access tool 304 in an axially slidable condition. Cannula 302 may have a sharpened, tapered, or beveled leading edge 502, such that it can be inserted easily into tissue.

In some embodiments, cannula 302 has a circular cross-section, such that a correspondingly shaped nucleotomy tool 304 may be freely rotated about its axis of extension. In other embodiments, cannula 302 may alternatively have a non-circular cross-section, for example a square, oval, polygon, or irregular shape, such that an appropriately shaped nucleotomy tool 304 may be partially rotatable within the cannula, or not rotatable at all. In further embodiments, cannula 302 may have a first cross-sectional shape, and nucleotomy tool 304 may have a different, second cross-sectional shape such that nucleotomy tool 304 may fully or partially rotate within cannula 302. The relationship of the first and second cross-sectional shapes can be arranged such that nucleotomy tool 304 is only rotatable through a defined range of motion (e.g., about 15 degrees or less, about 30 degrees or less, about 45 degrees or less, about 60 degrees or less, about 90 degrees or less, about 180 degrees or less, about 360 degrees or less). In this manner, movement of nucleotomy tool 304 is limited to a pre-defined range of motion, preventing inadvertent injury to healthy surrounding tissue, such as the vertebra above and below the intervertebral disc.

Nucleotomy tool 304 is illustrated as an axially extending rod having three channels 504, 506, and 508 extending from proximal access orifice 510 to a radially positioned distal access orifice 512. Distal end 534 can be generally shaped into a point, a blade, a spade, or a blunt end. Each of the channels 504, 506, and 508 of nucleotomy tool 304 is self-contained, such that the contents of each channel is separated from the contents of the others channels except at access orifices 510 and 512.

In some embodiments, distal end 534 may be of a beveled, tapered, or rounded point. In some embodiments, channels 504, 506, and 508 may of a circular, ovular, elliptical, polygonal, or irregular shaped cross-section. The cross section of each channel 504, 506, or 508 may be similar to that of the other channels, or may be of differing arrangements. Access orifices 510 and 512 are illustrated as roughly circular in shape. In some embodiments, access orifices 510 and 512 may be of differing shapes, such as ovals, ellipses, polygons, or irregular shapes.

Channel 504 is adapted to hold an appropriately dimensioned evacuation element 308. Evacuation element 308 includes one or more evacuation components, such as Archimedes screws 514 connected to connecting shaft 516. Shaft 516 is connected to and passes through the center of evacuation components 514 such that a continuous axial rotation of connecting shaft 516 results in a corresponding continuous rotation of evacuation components 514. Evacuation components 516 may be of an Archimedean screw or screw pump design, such that rotation of the element 516 can draw material through channel 504. Connecting shaft 516 may be connected on one end to a motorized drive (not shown), such that the connecting shaft 516 may be controllably rotated about its axis.

In some embodiments, evacuation components 514 may extend across the entire length of channel 504, or may extend across only a portion of channel 504. In some embodiments, there may be one or more evacuation components or multiple evacuation components 514. In some embodiments, evacuation components 514 and connecting shaft 516 are not present. In some embodiments, channel 504 may be connected to a vacuum pump, such that material is drawn through channel 504 by vacuum or suction. Connecting shaft 516 may be of a stiff material, such that it does not bend. In some embodiments, connector element may instead be of a flexible material, such that it is bendable. In these embodiments, the connecting shaft may still be rotated such to drive the rotation of evacuation elements 514.

Channel 506 is adapted to hold an appropriately dimensioned maceration tool 306. Maceration tool 306 includes a maceration basket 518 and a maceration shaft 520. Maceration basket 518 and maceration shaft 520 are connected such that axial rotation of maceration shaft 520 results in a corresponding rotation of maceration basket 518. Maceration basket 518 is of a whisk-like design, such that its rotation causes the maceration of contacted material. Edges of maceration basket 518 may also be sharpened to provide more effective maceration. Maceration basket 518 is of an expandable-collapsible design, such that it expands from a low-profile configuration while within channel 506 to an expanded-profile configuration when removed from channel 506 (illustrated in high-profile configuration in FIG. 5).

Maceration shaft 520 may be connected on one end to a motorized drive (not shown), such that the maceration shaft 520 may be controllably rotated about its axis. Maceration shaft 520 is of a bendable memory material, such that it may bend when sufficient force is applied, but will retain its original shape when force is removed. Sufficient shape memory materials include Nichol-titanium alloys and shape memory polymers. Axially moving maceration shaft 520 along channel 506 pushes maceration basket 518 along channel 506. Upon reaching curved wall portion 522 at the distal end of channel 506 and generally adjacent or proximate to distal point 514, maceration basket 518 and maceration shaft 520 will be directed in a direction 524, distal access orifice 512 in a direction generally orthogonal to the axial extension of access tool 300. Pushing maceration shaft 520 in a proximal to distal direction causes maceration basket 518 to continue in direction 524. Pulling maceration shaft 520 in a distal to proximal direction causes maceration element 518 to retract, first in a direction opposite direction 524, then back into distal orifice 512 and back up channel 506.

Connector 520 is connected to knob 526, which is configured to control the extension or retraction of maceration shaft 520 and maceration basket 518. In some embodiments, connector 520 may be wound around spindle 528, such that rotating knob 526 controllably moves maceration shaft 520 along channel 506. Knob 526 is rotatable to predefined stops, such that rotating knob 526 to each stop moves maceration shaft 520 and maceration basket 518 by a predetermined length. The predetermined length may correspond to approximately the width W of maceration basket 518. In this manner, the knob 526 may be predictably rotated in a step-wise manner such that maceration basket 518 is deployed out of distal orifice 512 and covers the full radial range of the maceration basket 518 without significant overlap between stops.

In some embodiments, maceration basket 518 is of a self-expanding memory design, such that it will self-expand to a predetermined dimension upon exiting channel 506. In other embodiments, maceration basket 518 is of a controllably-expandable design, such that it may be manually changed from a one or more low-profile configurations to one or more expanded-profile configurations. In some embodiments, maceration basket 518 may instead be in a configuration other than that of a whisk. Alternative configurations may include a pinwheel, propeller, a screw, a paddle, or fan-like design. In some embodiments, knob 526 may be replaced by a switch, ratcheting mechanism, or other discretely controllable mechanism. In some embodiments, knob 526 may be continuously rotatable without predetermined stops, such that the extension of maceration tool 306 may be freely adjusted.

Channel 508 is connected to a pump (not shown) such that irrigating liquid can be forced down the channel 508 and into the intervertebral disc 108 in the form of stream 310. Liquids may include water, saline, radiopaque substance, a gel, cement, silicone, or an epoxy. The pump may pump liquid in a continuous stream, in a pulsating stream, or switched off entirely. The pump may be adjusted to control flow rate and pressure of stream 310 may be adjusted during operation. Channel 508, curve 522, and end 514 are shaped such that stream 310 is directed in a direction parallel of direction 524, such that stream 310 contacts and is dispersed by maceration basket 518. The pump may include certain control elements such that maximum volumes of fluid may not be exceeded, or that delivery of fluid must be coordinated with the evacuation of the fluid via the suction provide through channel 504.

Maceration tool 306 and evacuation tool 308 may be operated simultaneously or independently. If connection shaft 516 and maceration shaft 520 are connected to separate drive mechanisms, each of the drives may work independently of the other, such that the speed of operation of each may differ during use. One drive may also be shut off independently over the other, such that only maceration or only evacuation occurs at a given time. Shafts 516 and 520 may also be connected to the same drive, such that they are rotated simultaneously. The drive may include independent gearing for each element, such that one element may be operated and adjusted independently of the other element.

Portions of nucleus removal device 300 may be made of various materials, such as metal, plastic, acrylic, or glass. Device 300 may be made of surgically compatible materials, such that they can be safely used in a sterile environment. Some portions of device 300 may be made of a radiopaque material, such that they provide imaging contrast during x-ray or fluoroscopic procedures. Device 300 may be made of non-ferrous materials, such that they are usable in conjunction with magnetic resonance imaging. Portions of device 300 may be made of paramagnetic or super paramagnetic materials, such that they provide imaging contrast during MRI.

In some embodiments, components of device 300 are detachably connected, such that each of the components may be independently removed, cleaned, and replaced. In some embodiments, portions of device 300 are designed to be disposable, while other portions are designed to be repeatedly reused.

The device may also be used to remove tissue from other portions of the body, and is not limited only in removing nuclear pulposus from an intervertebral disc.

A number of embodiments of the invention have been described. Nevertheless, it will be understood that various modifications may be made without departing from the spirit and scope of the invention. Accordingly, other embodiments are within the scope of the following claims.

Figure 7:
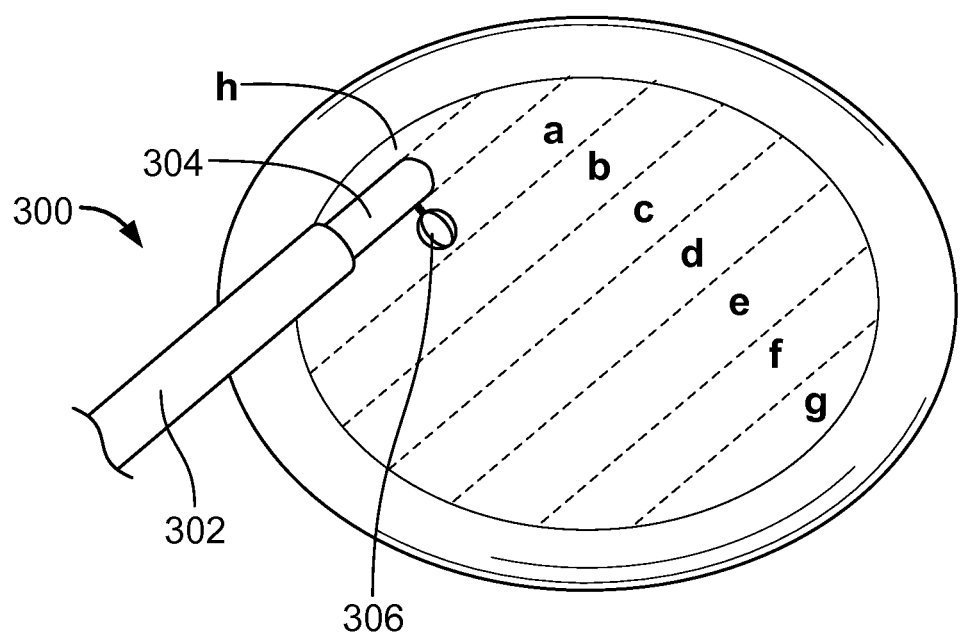
FIG. 7 illustrates an additional example use of an embodiment of a nucleus removal tool.
Figure 8A:
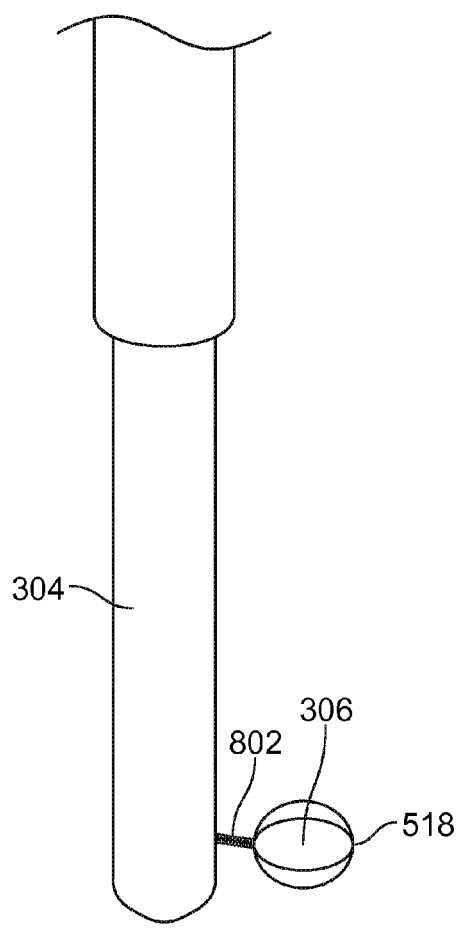
FIGS. 8A-D illustrate embodiments of an access tool with an articulating maceration element.
Figure 8B:
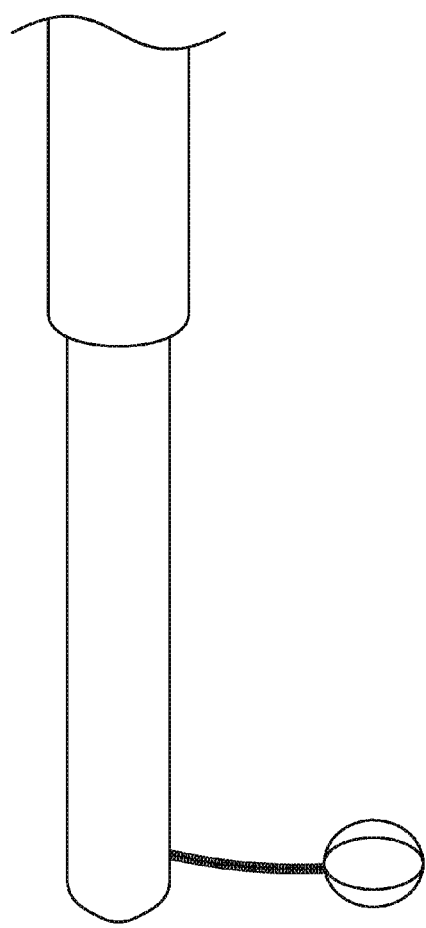
Figure 8C:
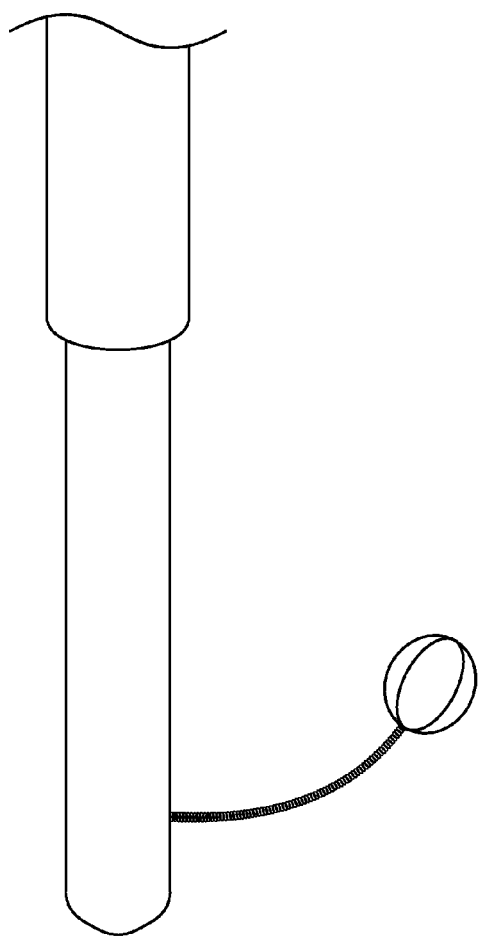
Figure 8D:
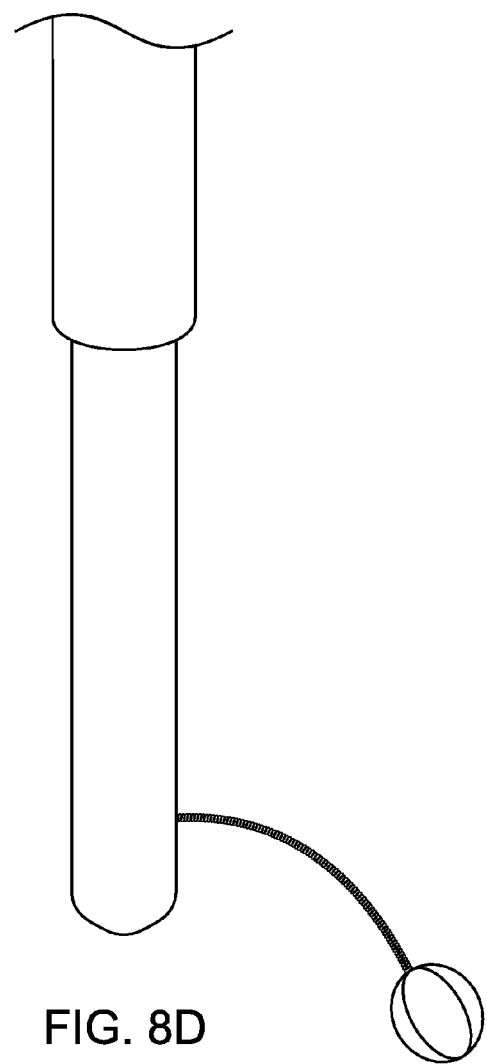

For example, nucleus removal device 300 is depicted as being inserted such that it passes through the center point of intervertebral disc 108. This need not be the case. In some implementations, nucleus removal device 300 is inserted in an off-center position, such that nucleus removal device 300 passes through only an outer portion of intervertebral disc 108. In some implementations, nucleus removal device 300 may be inserted in an oblique direction. In these implementations, maceration tool 306 may be extended to access all portions of nucleus pulposis 204. FIG. 7 illustrates an example off-center and/or oblique insertion of nucleus removal device 300 in intervertebral disc 108. In this instance, nucleotomy tool 304 may axially slide within access cannula 302 such that maceration element 306 macerates a portion (a) of nucleus pulposis 204. Maceration element 306 may be extended to access additional portions (a-g) of nucleus pulposus 204, nucleotomy tool 304 may be rotated to access other additional portions (h).

In some embodiments, a portion of maceration element 306 is housed in a flexible housing 802, as illustrated in FIG. 8. Housing 802 may be of a flexible material, such as a textile braid or a flexible metal, such that the orientation of maceration element 518 may be adjusted. Housing 802 may also be of memory material, such as nitinol or shape memory polymers, such that maceration basket 518 favors a pre-determined orientation. Housing 802 may be of an articulating design, such that the adjustment of maceration basket 518 may be controlled by a user during the operation of device 300. For example, as illustrated in FIG. 8, maceration basket 518 may be brought closer to (FIG. 8A) or further from (FIG. 8B) nucleotomy tool 304. Maceration basket 518 may also be drawn upward (FIG. 8C) or downward (FIG. 8D). (In this manner, maceration tool 306 may be adjusted to access a broad range of material within intervertebral disc 108, such that large portions of nucleus pulposis 204 may be macerated and evacuated from a single surgical insertion of device 300.

In another implementation the nucleus removal device 300 may comprise integrated channels performing one or more function. For example, irrigation or suction may be applied to the same channel that the nucleotomy tool occupies. Irrigation and suction may be supplied alternatively through the same channel. Or irrigation, suction and the nucleotomy tool may be supplied through one channel. In such alternative embodiments, irrigation, maceration, and suction may be operated in intervals depending on the availability of the shared channel.

In a further exemplary implementation of the present invention, an access cannula is provided for enabling penetration and access to the intervertebral disc, including penetration of the annulus fibrosis and access to the nucleus pulposus. Access is provided from a postero-lateral approach. The access cannula has a configuration, including cross-sectional size and shape to accommodate the anatomical profile of the intervertebral disc, such as having a straight-oval cross-section.

In an implementation of the invention, the access cannula comprises a guide needle with a sharp pointed stylet, an obturator fitting within the guide needle, a series of telescopic elongated tubular dilators, wherein the access cannula fits over the widest diameter dilator.

The proximal end of the cannula is secured to the skin of the patient by an adjustable retaining ring, which fits over and around the access cannula. A tightening screw secures the access cannula to prevent displacement relative to the retaining ring and generally hold the access cannula in position during procedures performed with the access cannula, such as the removal of tissue and the implantation of prosthetic devices.

Figure 9A:
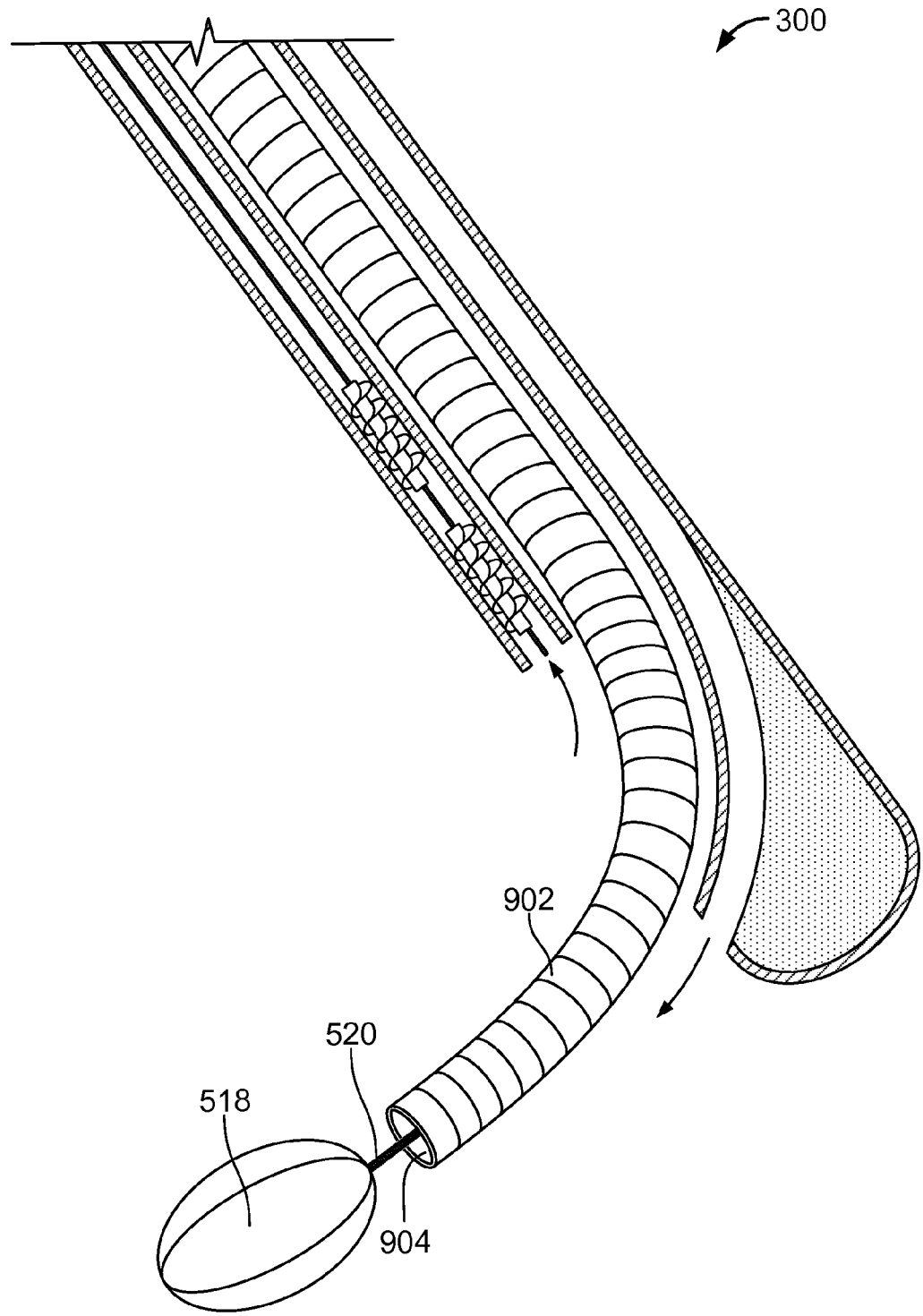
FIGS. 9A-B illustrate embodiments of nucleus removal tools.

In some embodiments, a portion of maceration shaft 520 may be covered by a catheter 902, as illustrated in FIG. 9A. Catheter 902 is generally tubular in shape, having a distal aperture 904 and a proximal aperture (not shown). Catheter 902 may be made of a memory material, such as nitinol or other shape memory alloy, or a shape memory polymer. In some embodiments, catheter 902 may be made of a textile, a polymer, a metal, or a composite material. When maceration shaft 520 and maceration basket 518 are extended or retracted from device 300, catheter 902 similarly extends or retracts to ensure that the same portion of maceration shaft 520 remains covered.

In some embodiments, various interchangeable catheters 902 are provided. The catheter 902 may have distal segments that possess memory features of acute or obtuse angles in order to reach all areas within the disc space.

Figure 9B:
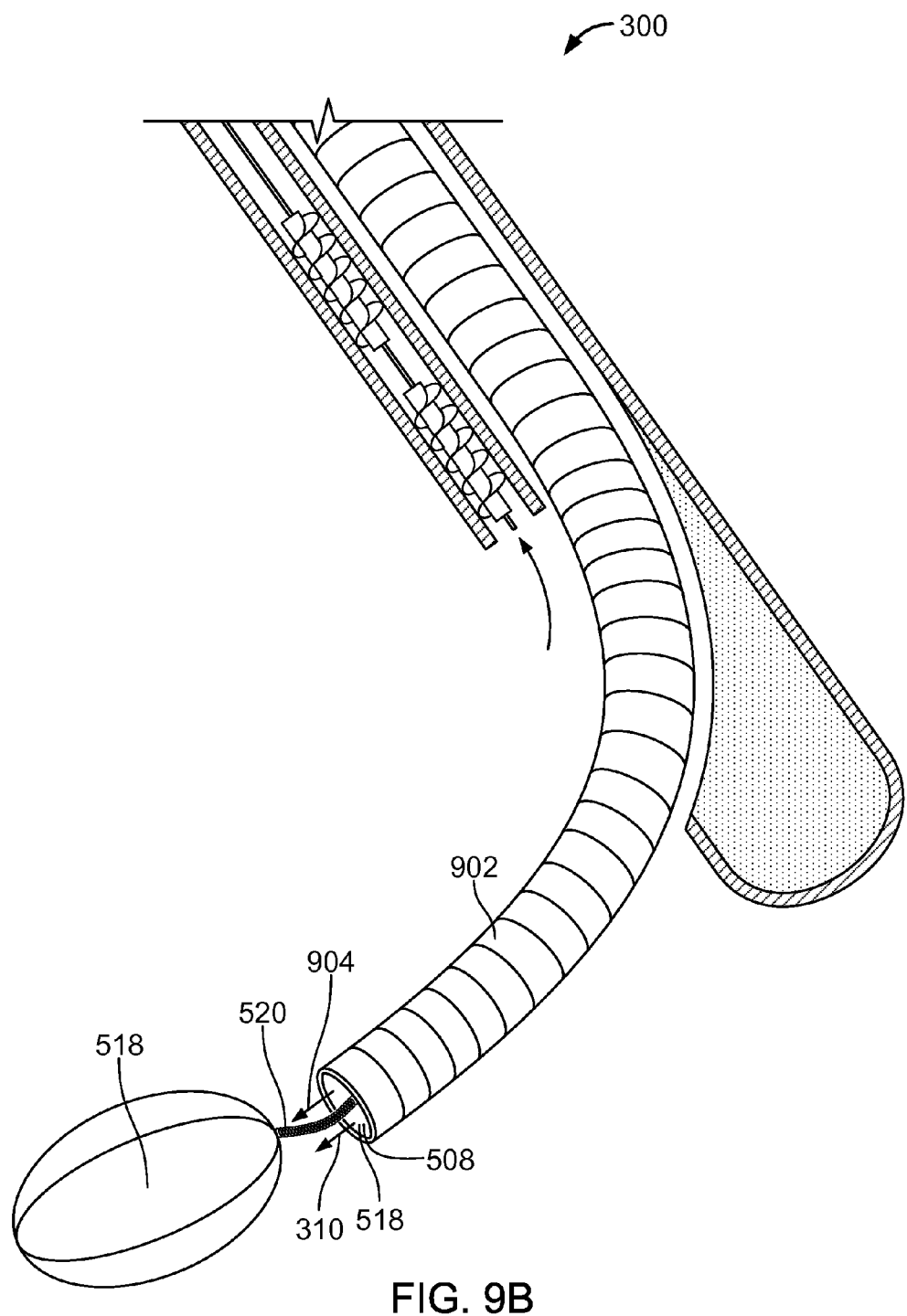

In some embodiments, channel 508 may also be located within catheter 902, as illustrated in FIG. 9B. In these embodiments, channel 508 carries stream of liquid 310, and stream of liquid 310 is expelled from aperture 904 of catheter 902 and towards maceration basket 518. As catheter 902 extends or retracts along with maceration shaft 520 and maceration basket 518, aperture 904 remains approximately the same distance from maceration basket 518, regardless of the distance of extension of maceration basket 518. In this manner, stream of liquid 310 is directed towards maceration basket 518 regardless of the orientation of maceration basket 518.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims.

What is claimed is:
1. An apparatus comprising:
an axially extending tubular access tool, comprising:
    a proximal first end having a first orifice along the axial extension of the tool,
    a distal second end, forming a point along the axial extension of the tool,
    a second orifice, formed between the first end and the second end and located on an axis orthogonal to the axial extension of the cannula,
    a first tubular channel extending from the first orifice to the second orifice, adapted to channel a liquid from the first orifice to the second orifice,
    a second tubular channel extending from the first orifice to the second orifice and in cooperative arrangement with a maceration tool,
    a third tubular channel extending from the first orifice to the second orifice and in cooperative arrangement with an evacuation tool;
a maceration tool within the second channel, comprising a maceration element and a first axially extending shaft, wherein radial rotation of the first shaft results in rotation of the maceration element;

an evacuation tool within the third channel, comprising one or more evacuation elements and a second axially extending shaft, wherein radial rotation of the second shaft results in rotation of the evacuation element;

wherein movement of the first shaft in a proximal to distal direction results in movement of the maceration element out of the second orifice in a direction generally orthogonal to the longitudinal extension of the tubular access tool;

wherein the maceration element is adapted to macerate tissue when rotated; and wherein the evacuation elements are adapted to move material through the third channel when rotated.

2. The apparatus of claim 1, further comprising:
an axially extending access cannula, comprising:
   a distally located first end, forming a first access hole along the axial extension of the cannula, a proximally located second end, forming a second access hole along the cannula,
   a tubular channel extending form the first access hole of the cannula to the second access hole of the cannula, wherein the tubular channel of the cannula is adapted to receive the access tool.

3. The apparatus of claim 1, wherein the maceration tool is self-expanding.

4. The apparatus of claim 1, wherein the first or second shaft is connected to a motorized drive.

5. The apparatus of claim 1, wherein the first channel is connected to a liquid pump.

6. The apparatus of claim 1, wherein an axial cross section of the tubular access tool is of a generally polygonal, ovular, circular, or elliptical shape.

7. The apparatus of claim 1, wherein the device comprises a surgically compatible material.

8. The apparatus of claim 1, wherein device of the apparatus comprises a radiopaque material.

9. The apparatus of claim 1, wherein the cannula is adapted to be percutaneously inserted into an intervertebral disc.

10. An apparatus for removing a portion of a nucleus pulposus, comprising:
   a maceration tool comprising a maceration element coupled to a first shaft, wherein rotation of the first shaft rotates the maceration element;
   an evacuation tool comprising one or more evacuation elements and a second shaft, wherein rotation of the second shaft rotates the one or more evacuation elements;
   an access tool extending from a proximal end to a distal end, comprising:
      a maceration tool channel extending from the proximal end to the distal end of the access tool for slidably receiving the maceration tool, wherein movement of the maceration tool in a proximal to distal direction extends the maceration element out of the distal end of the access tool in a direction generally orthogonal to a longitudinal axis of the access tool;
      an evacuation channel extending from the proximal end to the distal end of the access tool for receiving the evacuation tool;
   wherein the maceration element is adapted to macerate tissue when rotated; and
   wherein the one or more evacuation elements are adapted to evacuate material through the evacuation channel when rotated.

11. The apparatus of claim 10, wherein the one or more evacuation elements comprise Archimedes screws.

12. The apparatus of claim 11, wherein the second shaft comprises a flexible material.

13. The apparatus of claim 10, further comprising an irrigation channel extending from the proximal end to the distal end of the access tool for delivering irrigation fluid to the distal end of the access tool.

14. The apparatus of claim 10, wherein the maceration tool further comprises a flexible housing for receiving the rotating shaft.

15. The apparatus of claim 14, wherein the flexible housing is articulatable.

16. The apparatus of claim 10, further comprising a catheter for covering at least a portion of the first shaft.

* * * * *